United States Patent
Wang et al.

(10) Patent No.: US 7,810,396 B2
(45) Date of Patent: Oct. 12, 2010

(54) TEST DEVICE FOR ELECTRONIC PRODUCT

(75) Inventors: J. J. Wang, Shanghai (CN); Li-Min Sun, Shanghai (CN)

(73) Assignee: Inventec Appliances Corp., Taipei (TW)

( * ) Notice: Subject to any disclaimer, the term of this patent is extended or adjusted under 35 U.S.C. 154(b) by 168 days.

(21) Appl. No.: 12/315,909

(22) Filed: Dec. 8, 2008

(65) Prior Publication Data

US 2009/0145240 A1   Jun. 11, 2009

(30) Foreign Application Priority Data

Dec. 6, 2007   (TW) .............................. 96146624 A

(51) Int. Cl.
*G01N 3/08* (2006.01)
(52) U.S. Cl. .............................. 73/818; 73/760; 73/856
(58) Field of Classification Search ............ 73/760–818
See application file for complete search history.

(56) References Cited

U.S. PATENT DOCUMENTS 6,452,502 B1 *   9/2002   Dishongh et al. ........... 340/653
6,546,294 B1 *   4/2003   Kelsey et al. ................. 700/27
2005/0077122 A1 *   4/2005   Harris et al. ............... 188/71.1

* cited by examiner

*Primary Examiner*—Max Noori
(74) *Attorney, Agent, or Firm*—Hudak, Shunk & Farine Co. LPA

(57) ABSTRACT

A test device for an electronic product includes a vertical pressing pole having a pushing end. The test device also includes a movable platform with a sticking point, wherein upward movement of the movable platform moves the vertical pressing pole upwards by the sticking point. The vertical pressing pole passes through a balance weight which rests on the sticking point. A pressurized platform bears pressure from the pushing end, when the pushing end is pushed onto the pressurized platform. A load-bearing platform supports the pressurized platform and the electronic product located below the pressurized platform. The product is pressed between the pressurized platform and the load-bearing platform due to the pressure from the pushing end lying on the pressurized platform. When the movable platform is further moved downwards after the pushing end is on the pressurized platform, the sticking point bearing the balance weight is separate from the movable platform.

13 Claims, 2 Drawing Sheets

TEST DEVICE FOR ELECTRONIC PRODUCT

BACKGROUND OF THE INVENTION (a) Field of the Invention

The present invention relates to a test device, and more particularly to a test device capable of performing high-precision testing for an electronic product by the interlocking action of a force controllable vertical pressing pole, a pressure platform and a limiting position slice.

(b) Description of the Prior Art

Presently, as the electronic product technology is becoming more and more mature, the structures of electronic products have higher and higher precision. Great importance is attached to the reliability tests of electronic products, among which a pressing test and a pulling/pushing test are the two most important items.

In the prior art, the test apparatus with lower precision shown in FIG. 1 is mostly used in the reliability tests. Such apparatus employs active and integrated transmission, and it transforms power from a motor into a push-pull force in the horizontal direction through a turbine 11, and the push-pull force directly acts on a device under test. Such conventional test apparatus has three shortcomings as follows:

A. the turbine shaft 111 has low precision due to the limitation of the anti-friction design and the mechanical lever self-design (about 0.5 mm of die tolerance), so the transformation of horizontal pushing force is difficult to achieve 1 mm;

B. With the horizontal push rod 12 directly acting on a sample under test, it is unable to control the force and easy to cause accidental damage to the sample and the tester; and C. After a period of use, the turbine shaft wears out significantly will directly lead to a marked reduction in the precision of the tester as well as it is hard to improve through calibration.

Besides, there are high-precision insertion testers in prior art, but there are still some drawbacks as follows:

A. Such tester is precise but expensive, with a finite life, so the cost per testing is very high; and B. The carrier of the tester can hold only one sample for one time, hence its low utilization rate increases the time that a test takes.

SUMMARY OF THE INVENTION

In view of the above-mentioned circumstances, an objective of the present invention is to provide a test device for an electronic product to solve the problems of high cost and insufficient precision occurred in a reliability test.

For the objective of the present invention, a test device for testing the reliability of an electronic product is disclosed, and the test device comprises a vertical pressing pole, a movable platform with a sticking point, a balance weight, a pressurized platform and a load-bearing platform. The vertical pressing pole comprises a pushing end. The movable platform comprises a first opening, and the vertical pressing pole passes through the first opening and sticks to the sticking point so that upward movement of the movable platform moves the vertical pressing pole upwards by the sticking point. The balance weight comprises a second opening through which the vertical pressing pole passes and the balance weight resting on the sticking point. The pressurized platform is used to bear the pressure from the pushing end of the vertical pressing pole when the pushing end is pushed onto the pressurized platform due to downward movement of the movable platform. The load-bearing platform supports the pressurized platform by a plurality of positioning stems connected between the load-bearing platform and the pressurized platform, and supports the electronic product located below the pressurized platform. The electronic product is pressed between the pressurized platform and the load-bearing platform due to the pressure from the pushing end lying on the pressurized platform; and when the movable platform is further moved downwards after the pushing end is on the pressurized platform, the sticking point bearing the balance weight is separate from the movable platform.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PREFERRED EMBODIMENTS

Exemplary embodiments of the present invention are described herein in the context of a test device for an electronic product.

Those of ordinary skill in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings. The same reference indicators will be used throughout the drawings and the following detailed description to refer to the same or like parts.

Figure 1:
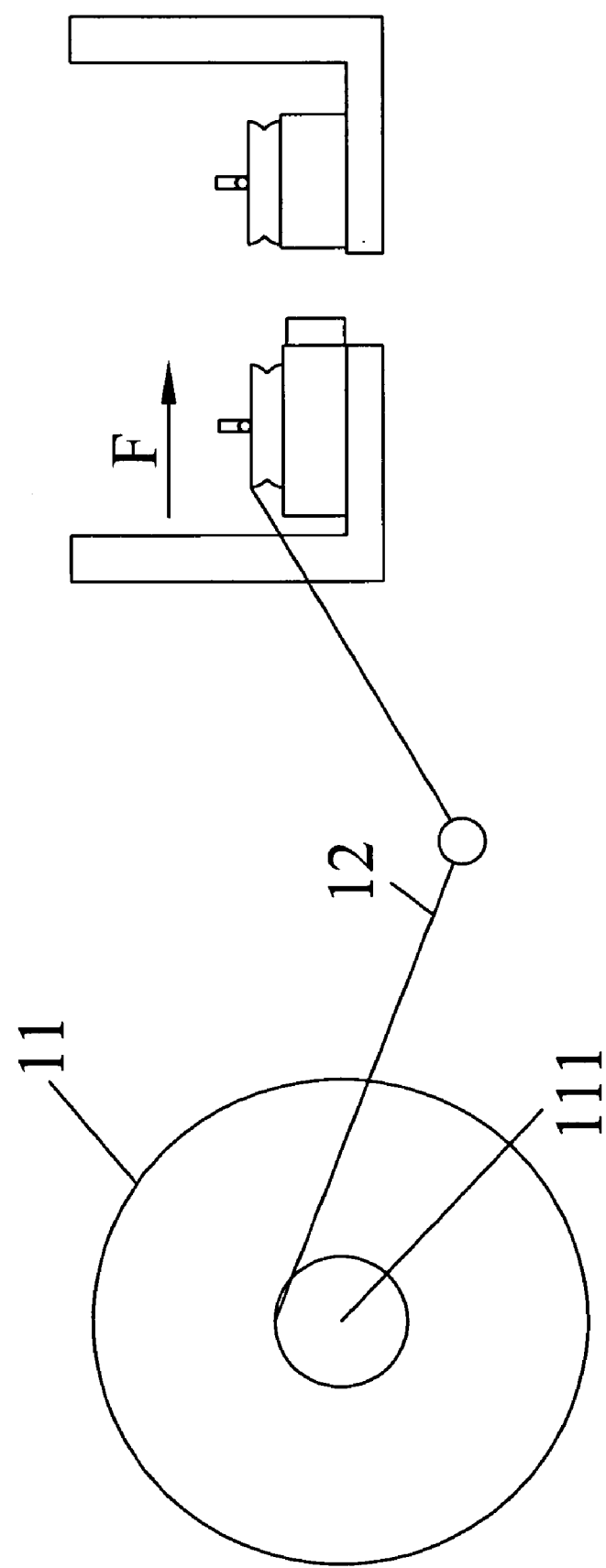
FIG. 1 is a schematic view showing a test instrument with active and integrated transmission of the prior art.
Figure 2:
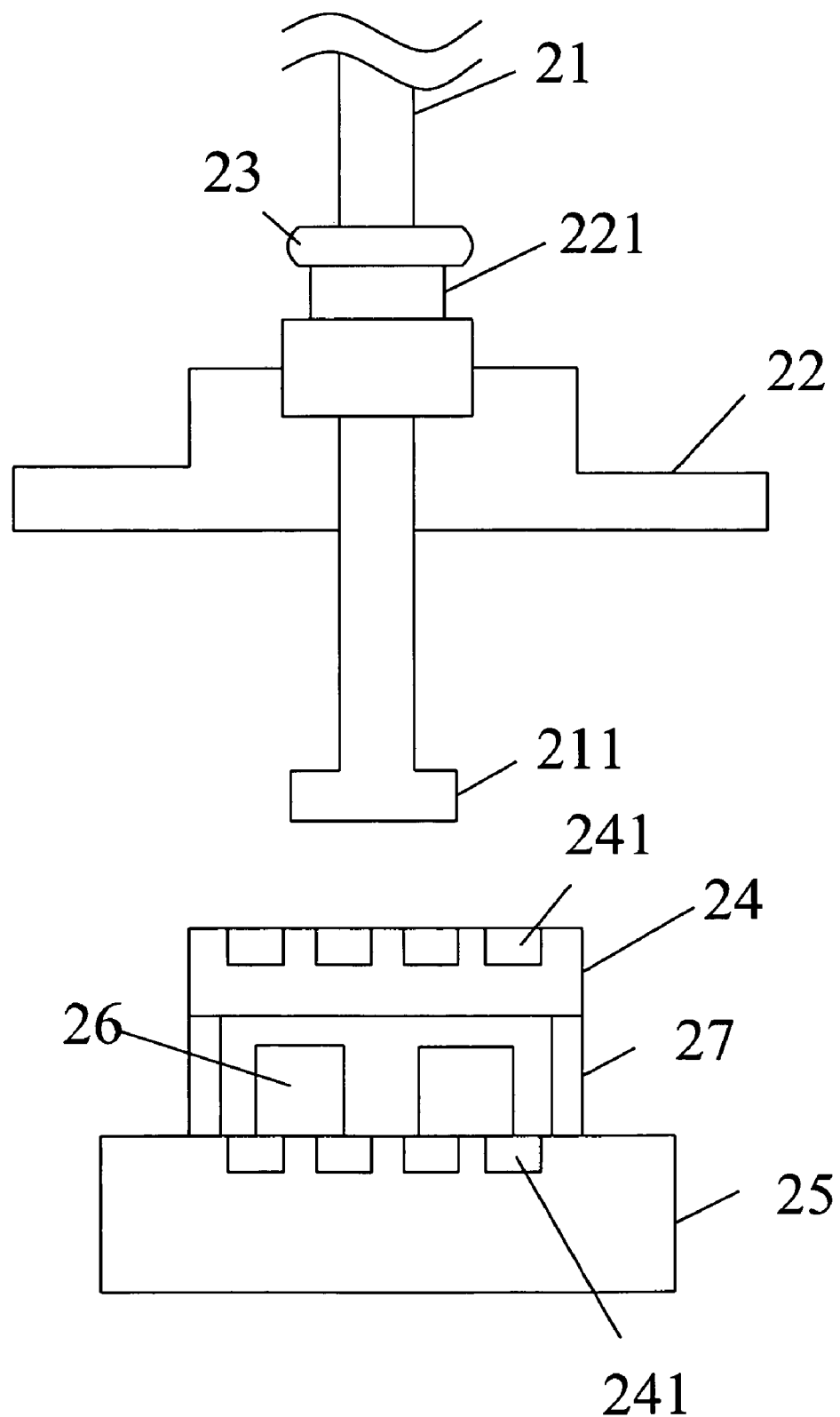
FIG. 2 is a schematic view showing a test device for an electronic product according to an embodiment of the present invention.

FIG. 2 illustrates a schematic view showing a test device for an electronic product according to an embodiment of the present invention. The test device in the drawing is used to test the reliability of an electronic product, and comprises a vertical pressing pole 21, a movable platform 22, a balance weight 23, a pressurized platform 24 and a load-bearing platform 25. The vertical pressing pole 21 comprises a pushing end 211. The movable platform 22 is with a sticking point 221 and comprises a first opening. The vertical pressing pole 21 passes through the first opening and sticks to the sticking point 221. Preferably, the vertical pressing pole can further comprise a salient point and stick to the sticking point 221 by the salient point.

The movable platform 22 can be electrically connected to a motor so as to drive the vertical pressing pole 21 to move up and down by an external driving force. When the movable platform 22 ascends by a force, the sticking point 221 of the movable platform 22 is connected to the salient point of the vertical pressing pole 21, and is thus capable of driving the vertical pressing pole 21 to move upwards. In other words, upward movement of the movable platform 22 moves the vertical pressing pole 21 upwards by the sticking point 221.

The balance weight 23 comprises a second opening through which the vertical pressing pole 21 passes and the balance weight 23 rests on the sticking point 221. When the movable platform 22 is further moved downwards after the pushing end 211 is on the pressurized platform 24, the sticking point 221 bearing the balance weight 23 is separate from the movable platform. When the sticking point 221 bearing the balance weight 23 is separate from the movable platform 22, the pressure borne by the pressurized platform 24 is substantially determined by the vertical pressing pole 21 and the balance weight 23.

The pressurized platform 24 is used to bear the pressure from the pushing end 211 of the vertical pressing pole 21. While the movable platform 22 is moved downwards by a force, the pushing end 211 of the vertical pressing pole 21 is pushed onto the surface of the pressurized platform 24 and subsequently the sticking point 221 bearing the balance weight 23 is separated from the movable platform 22 with the movable platform 22 continuing to descend. The pressure borne by the pressurized platform 24 is substantially determined by the vertical pressing pole 21 and weight of the balance weight 23, and is applied to the pressurized platform 24 through the vertical pressing pole 21 to generate a pressing action between the pressurized platform 24 and the load-bearing platform 25, such that the electronic product is pressed between the pressurized platform 24 and the load-bearing platform 25 due to the pressure from the pushing end 211 lying on the pressurized platform 24.

The load-bearing platform 25 supports the pressurized platform 24 by a plurality of positioning stems 27 connected between the load-bearing platform 25 and the pressurized platform 24 and supports the electronic product located below the pressurized platform 24. The positioning stem 27 combines with a spring to elastically reset the pressurized platform 24 to an original position after the pressure from the pushing end is reduced. At least one limiting position slice 26 which also serves as a pressing-distance-limiting slice, is disposed between the load-bearing platform 25 and the pressurized platform 24 to adjust the pressing distance of the test device, It means that the pressing distance between the pressurized platform and the load-bearing platform when the electronic product is pressed by the pressurized platform is substantially not less than a height of at least a pressing-distance-limiting slice placed on the load-bearing platform 25. When the pressurized platform 24 is pressed to the limited height, the limiting position slice 26 supports the pressurized platform 24 to complete the pressing operation; in other words, the pressurized platform 24 is pressed by the pushing end 211 downwards only until the pressurized platform 24 touches against the limiting position slice 26 placed on the load-bearing platform 25. The number of the limiting position slices 26 can be increased or decreased to accurately calibrate the pressing distance between the load-bearing platform 25 and the pressurized platform 24; in other words, the pressing distance is adjustable for precision by adjusting the number of the pressing-distance-limiting slices.

At least one socket 241 is disposed on the pressurized platform 24 or the load-bearing platform 25 for holding and fixing the position of the electronic product. Preferably, the socket 241 can be electrically connected to a sensor for sensing the presence of the electronic product, and different types or sizes of the socket 241 are suitable for satisfying test requirements of different types or sizes of the electronic product.

With the movable platform 22 ascending, the salient point of the vertical pressing pole 21 is engaged with the sticking point 221 of the movable platform 22 once more. The spring force enables the pressurized platform 24 and the load-bearing platform 25 to return their original positions and separate from the electronic product under test, so as to complete one pressing operation.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded interpretation so broad as to encompass all such modifications and similar arrangements and procedures.

What is claimed is:

1. A test device for testing the reliability of an electronic product, comprising:
   a vertical pressing pole comprising a pushing end;
   a movable platform with a sticking point, the movable platform comprising a first opening, the vertical pressing pole passing through the first opening and sticking to the sticking point so that upward movement of the movable platform moves the vertical pressing pole upwards by the sticking point;
   a balance weight comprising a second opening through which the vertical pressing pole passes, the balance weight resting on the sticking point;
   a pressurized platform for bearing pressure from the pushing end of the vertical pressing pole, when the pushing end is pushed onto the pressurized platform due to downward movement of the movable platform; and
   a load-bearing platform supporting the pressurized platform by a plurality of positioning stems connected between the load-bearing platform and the pressurized platform, and supporting the electronic product located below the pressurized platform;
   wherein the electronic product is pressed between the pressurized platform and the load-bearing platform due to the pressure from the pushing end lying on the pressurized platform; and when the movable platform is further moved downwards after the pushing end is on the pressurized platform, the sticking point bearing the balance weight is separate from the movable platform.

2. The test device of claim 1, wherein a pressing distance between the pressurized platform and the load-bearing platform when the electronic product is pressed by the pressurized platform is substantially not less than a height of at least a pressing-distance-limiting slice placed on the load-bearing platform.

3. The test device of claim 2, wherein the pressing distance is adjustable for precision by adjusting the number of the pressing-distance-limiting slices.

4. The test device of claim 1, wherein at least one of the plurality of positioning stems combines with a spring to elastically reset the pressurized platform to an original position after the pressure from the pushing end is reduced.

5. The test device of claim 1, wherein at least a socket is disposed on the pressurized platform for holding and fixing the position of the electronic product.

6. The test device of claim 5, wherein the socket is electrically connected to a sensor for sensing the presence of the electronic product.

7. The test device of claim 5, wherein different types or sizes of the socket are suitable for satisfying test requirements of different types or sizes of the electronic product.

8. The test device of claim 1, wherein at least a socket is disposed on the load-bearing platform for holding and fixing the position of the electronic product.

9. The test device of claim 8, wherein the socket is electrically connected to a sensor for sensing the presence of the electronic product.

10. The test device of claim 8, wherein different types or sizes of the socket are suitable for satisfying test requirements of different types or sizes of the electronic product.

11. The test device of claim 1, wherein the pressurized platform is pressed by the pushing end downwards only until the pressurized platform touches against a pressing-distance-limiting slice placed on the load-bearing platform.

12. The test device of claim 1, wherein the vertical pressing pole comprises a salient point and sticks to the sticking point by the salient point.

13. The test device of claim 1, wherein when the sticking point bearing the balance weight is separate from the movable platform, the pressure borne by the pressurized platform is substantially determined by the vertical pressing pole and the balance weight.

* * * * *